United States Patent [19]

Grasselli et al.

[11] 4,065,468

[45] Dec. 27, 1977

[54] MANUFACTURE OF MALEIC ANHYDRIDE FROM BUTANE

[75] Inventors: Robert K. Grasselli, Cleveland; Dev D. Suresh, Macedonia; Robert C. Miller, Northfield, all of Ohio

[73] Assignee: Standard Oil Company, Cleveland, Ohio

[21] Appl. No.: 685,879

[22] Filed: May 12, 1976

Related U.S. Application Data

[63] Continuation of Ser. No. 67,269, Aug. 26, 1970, abandoned.

[51] Int. Cl.$^2$ ............................................. C07D 307/60
[52] U.S. Cl. .............................. 260/346.75; 252/432; 252/435; 252/437; 252/439; 252/456; 252/467; 252/470
[58] Field of Search ................................ 260/346.8 A

[56] References Cited

U.S. PATENT DOCUMENTS 2,691,660   10/1954   Hartig ........................... 260/346.8 A

FOREIGN PATENT DOCUMENTS 1,157,117   7/1969   United Kingdom.

Primary Examiner—Henry R. Jiles
Assistant Examiner—Bernard Dentz
Attorney, Agent, or Firm—Gwenetta Douglas Hill; Herbert D. Knudsen; Larry W. Evans

[57] ABSTRACT

Maleic anhydride is produced by the reaction of n-butane with a molecular oxygen-containing gas at an elevated temperature in the presence of a catalyst composed of the combined oxides of the elements antimony, molybdenum and at least one member selected from the group consisting of iron and vanadium and optionally one or more oxides of aluminum, boron, tellurium, chromium, cobalt, nickel, copper, bismuth, phosphorus titanium and tungsten.

11 Claims, No Drawings

MANUFACTURE OF MALEIC ANHYDRIDE FROM BUTANE

REFERENCE TO RELATED APPLICATIONS

This is a continuation of our earlier application, Ser. No. 67,269, filed Aug. 26, 1970 and now abandoned.

This invention relates to a process for the production of maleic anhydride and more particularly pertains to the manufacture of maleic anhydride by the oxidation of paraffins in the presence of a catalyst comprising antimony, molybdenum, and at least one member selected from the group consisting of iron and vanadium.

According to the process of the present invention maleic anhydride is produced by the reaction of a paraffin hydrocarbon having from 4 to 5 carbon atoms with molecular oxygen or a molecular oxygen-containing gas at an elevated temperature in the presence of a catalyst composed of the combined oxides of the elements antimony, molybdenum and at least one member selected from the group consisting of the oxides of iron and vanadium, and optionally one or more of the oxides of aluminum, tellurium, chromium, cobalt, nickel, copper, bismuth, phosphorus, titanium and tungsten. The process of this invention is carried out in the gaseous phase and the solid catalyst may be used per se or on a support and may be either a fixed bed or fluid bed.

The preferred paraffinic hydrocarbons for the process of this invention are the butanes and most preferred is n-butane.

The catalyst employed in the process of this invention can be used alone or supported on or impregnated in a carrier material such as silica, alumina, zirconia, calcium-stabilized zirconia, thoria, boron phosphate, silicon carbide, pumice, clay, diatomaceous earth, or titania. In general, this support may be employed in amounts less than 95 percent by weight of the final catalyst composition.

The catalysts embodied herein may be calcined to produce desirable physical properties such as attrition resistance, optimum surface area and particle size. It is generally preferred that the calcined catalyst be further heat-treated in the presence of oxygen and at a temperature of above 500° F but below a temperature deleterious to the catalyst.

The process of this invention is carried out at a temperature in the range of 300° C to 600° C and preferably in the range of from 350° C to 500° C under a pressure of from about 1 to 500 psig and preferably from 10 to 100 psig.

In the process of this invention the molecular oxygen or molecular oxygen-containing gas should be present in the molar ratio of oxygen to paraffinic hydrocarbon of from 20:1 to 1:20, respectively. It is also contemplated to include steam in the feed to the reactor in the instant process and there may be present in the feed from 0 to 50 moles of steam per mole of the paraffinic hydrocarbon.

The apparent contact time in the instant process can be from 0.1 to 50 seconds and preferably from about 0.5 to 10 seconds.

The catalysts most useful in this invention are those having the formula $A_aB_bSb_cMo_dO_e$ wherein A is at least one member selected from the group consisting of iron and vanadium, B is at least one member selected from the group consisting of aluminum, chromium, cobalt, nickel, copper, bismuth, tellurium, boron, phosphorus, titanium and tungsten, $a$ is a number from 0.1 to 6, $b$ is a number from 0 to 3, $c$ is number from 0.1 to 12, $d$ is a number from 12 to 0.1, and $e$ is a number determined by the valence requirements of the combined valences of the elements other than oxygen present in the catalyst. The catalysts of this invention can be prepared by dissolving or slurrying salts of their respective metals in water or acid and heating the mixture with an aqueous silica dispersion until a gel forms. After gelation, the resulting mixture is heated at 130° C until dry. The catalyst is then heated at about 300° C for 4 hours and calcined at 800° F in air for an additional 24 hours. In some instances, the catalysts were also further treated in air for 3 hours at 1200° F.

The catalysts preferably are heat-treated in the presence of molecular oxygen in the range of about 800° F to 1600° F before they are employed in the present process.

The reactor employed for the conversion of butane to maleic anhydride was a standard reactor with a fixed catalyst bed. The catalyst volume was 5 cc and the catalyst mesh size was 20 to 35 per inch. The gases were metered with rotameters.

The product was analyzed by one or more methods. Two gas chromatographic methods were used. In the first gas chromatographic method a Fisher Gas Partitioner was used and the system for the Fisher Gas Partitioner is commonly referred to as Fisher System "D" which consists of two columns in series. Column A consisted of 6 feet of 30 percent hexamethylphosphoramide on Column pak D and was followed in series by Column B which is a combination column (5 feet of uncoated Column pak — 7 feet of molecular sieve 13X). The system was maintained isothermally at 30° C, and had a flow rate of 72.0 cc of He/minute. Standard gas mixtures were used for calibration of the system and plots for mole percent concentration vs. peak heights were obtained. The percent conversion of n-butane to $CO_2$ and CO was calculated by known procedures. The second gas chromatographic method was accomplished using an F&M model 5754A Gas Chromatograph System. A 2.0 meter × ⅜ inch Porapak-QS column maintained isothermally at 225° C was used in the system for separation of the components. Basically, a 5 microliter injection of the reaction product, maleic anhydride or acid, which was trapped in water was injected into the F&M system. The injection port was maintained at 305° C to decompose any maleic acid to the anhydride. After separation in the column, detection was attained with a Flame Ionization Detector which was maintained at 305° C. A peak was obtained at a retention time of 4.1 minutes and was identified as maleic anhydride. Standard concentrations of maleic anhydride and maleic acid in water were made and plots for concentration of maleic anhydride vs. peak area were obtained.

An ultraviolet method for analysis of the product for maleic anhydride or maleic acid in which the product was allowed to stand in water and the U.V. absorbance spectra for the liquid sample were obtained using a Perkin-Elmer 202 U.V.-VIS. Spectrophotometer. Samples were water solutions run in 1 cm. cells versus water alone in a reference cell. The spectra were recorded from 200–390 m μ. There was no sharp U.V. maximum; however, the method was worked out based on absorption at 295 m μ. A plot of absorbance at 295 m μ versus the number of moles of maleic acid or anhydride per 100 ml. of water gave a linear graph for the standard solutions. The amount of maleic acid or anhydride in the unknown was read off the graph and the yield was calculated as follows:

$$\frac{(\text{Moles MA}/100 \text{ ml. H}_2\text{O})}{(\text{Theoretical yield})} \times \frac{5 \text{ ml.}}{100 \text{ ml.}} \times 100 = \% \text{ MA}$$

A quantitative method of determination of maleic acid includes titration of one cc. of the product with a standardized 0.005 N aqueous solution of sodium hydroxide. A graph was made of volume of 0.005 N NaOH versus number of gram-mole maleic acid and maleic anhydride in 5 cc. of water, using standard solutions of maleic acid and maleic anhydride. A factor (reciprocal of the slope) of $(2.58 \times 10^{-5} \text{ gram mole})/\text{cc NaOH}$ was obtained. The yield was calculated in the following manner:

$$\frac{(\text{cc of 0.005 N NaOH}) (\text{Factor})}{(\text{Theoretical yield})} \times 100 = \% \text{ of maleic acid}$$

In the following examples which further illustrate our invention the amount of the various ingredients used are expressed in parts by weight unless otherwise indicated.

EXAMPLE I

A catalyst composed of 80 percent by weight of $VFeSb_3Mo_{12}O_{48}$ and 20 percent by weight of $SiO_2$ was prepared from a mixture of:

| | | | |
|---|---|---|---|
| 3.9 | g. | $NH_4VO_3$ | (0.033 mole V) |
| 13.5 | g. | $Fe(NO_3)_3 \cdot 9H_2O$ | (0.033 mole Fe) |
| 14.5 | g. | $Sb_2O_3$ | (0.100 mole Sb) |
| 60 | cc. | $HNO_3$ | (70 percent by weight aqueous solution) |
| 70.6 | g. | $(NH_4)_6Mo_7O_{24} \cdot 4H_2O$ | (0.400 mole Mo) |
| 66.4 | g. | Ludox AS (DuPont) | (30 percent aqueous solution of $SiO_2$) |

The antimony oxide was oxidized with the nitric acid on a hotplate with constant stirring for about 30 minutes. Water slurries or solutions of the other compounds listed above were then added with heating and stirring was continued until the mixture started to gel. The product was dried in and oven (270° F) overnight. The catalyst was then heat-treated in air at 800° F for 16 hours and then at 1200° F in air for 3 hours. The final catalyst was found to have a surface area of 17 square meters per gram.

In general, the single pass conversion of n-butane to maleic anhydride increases with on-stream time until an optimum which can be sustained is reached.

Maleic anhydride was produced from n-butane in a vapor phase reactor over a fixed bed of the catalyst described above. In this reaction a standard fixed bed 5 cc. upflow reactor was used and a temperature of 450° C was employed. The molar ratio of n-butane-to-air in the feed was 1.25 and an apparent contact time of 1 second was used with the following results.

| On-Stream Time (Hrs.) | Single Pass Mole % Conversion of N-Butane to Maleic Anhydride | Single Pass Weight % Conversion of N-Butane to Maleic Anhydride |
|---|---|---|
| 0.5 | 9.8 | 16.6 |
| 1 | 12.1 | 20.5 |
| 20 | 16.2 | 27.4 |
| 70 | 20.1 | 34.0 |

EXAMPLE II

A catalyst was prepared according to the procedure of Example I which had the following composition: 80 percent by weight $Fe_2Sb_3Mo_{12}O_{47}$ and 20 percent by weight of $SiO_2$. This catalyst was prepared from the following ingredients:

| | | | |
|---|---|---|---|
| 27.0 | g. | $Fe(NO_3)_3 \cdot 9H_2O$ | (0.067 mole Fe) |
| 14.5 | g. | $Sb_2O_3$ | (0.100 mole Sb) |
| 60 | cc. | $HNO_3$ | (70 percent by weight aqueous solution) |
| 70.6 | g. | $(NH_4)_6Mo_7O_{24} \cdot 4H_2O$ | (0.400 mole Mo) |
| 66.0 | g. | Ludox AS | (30 percent aqueous solution of $SiO_2$) |

The oven dried product was heat-treated in air at 800° F overnight and at 1200° F for 19 hours.

N-butane was converted to maleic anhydride employing the catalyst of this example and the conditions described in Example I. A single pass conversion of n-butane to maleic anhydride of 12.4 mole percent (21.0 percent by weight) was obtained after one hour on stream in the reactor.

EXAMPLE III

A catalyst having the composition 80 percent by weight of $V_2Sb_3Mo_{12}O_{49}$ and 20 percent by weight of $SiO_2$ was prepared by the procedure described in Example I from the following materials:

| | | | |
|---|---|---|---|
| 7.8 | g. | $NH_4VO_3$ | (0.067 mole V) |
| 14.5 | g. | $Sb_2O_3$ | (0.100 mole Sb) |
| 60 | cc. | $HNO_3$ | (70 percent by weight aqueous solution) |
| 70.6 | g. | $(NH_4)_6Mo_7O_{24} \cdot 4H_2O$ | (0.400 mole Mo) |
| 66.7 | g. | Ludox AS | (30 percent aqueous solution of $SiO_2$) |

The antimony oxide was oxidized in the nitric acid on a hotplate with constant stirring for 30 minutes. A water slurry of the ammonium vanadate was then cooled, followed by addition of the Ludox. Stirring and heating were continued until the mixture started to gel. The product was dried at 130° C, heat-treated in air at 800° F overnight and at 1200° F for 19 hours. The final catalyst was found to have a surface area of 20 square meters per gram.

The procedure described in Example I for preparing maleic anhydride from n-butane was repeated using the catalyst of this example. A single pass conversion of n-butane to maleic anhydride of 12.3 mole percent (20.8 percent by weight) was achieved after 1.0 hour on stream.

EXAMPLE IV

A catalyst having a composition of 80 percent by weight of $Mo_2FeVSb_6O_{25}$ and 20 percent by weight of $SiO_2$ was prepared according to the procedure of Example I from the following materials:

| | | | |
|---|---|---|---|
| 58.1 | g. | $Sb_2O_3$ | (0.4 mole Sb) |
| 230 | cc. | $HNO_3$ | (70 percent by weight aqueous solution) |
| 26.9 | g. | $Fe(NO_3)_3 \cdot 9H_2O$ | (0.067 mole Fe) |
| 7.8 | g. | $NH_4VO_3$ | (0.067 mole V) |
| 23.6 | g. | $(NH_4)_6Mo_7O_{24} \cdot 4H_2O$ | (0.133 mole Mo) |
| 79.3 | g. | Ludox AS | (30 percent aqueous solution of $SiO_2$) |

The catalyst was dried and heat-treated in air at 800° F for 16 hours and at 1200° F for 19 hours.

The foregoing catalyst was used in the production of maleic anhydride from n-butane according to the procedure of Example I. A single pass conversion of 15.2 mole percent of maleic anhydride (25.7 percent by weight) was achieved after 1 hour on stream.

EXAMPLE V

A catalyst having a composition of 80 percent by weight of $BFeVSb_3Mo_{12}O_{49}$ and 20 percent by weight of $SiO_2$ was prepared by the procedure of Example I from the following ingredients:

| 3.9 g. | $NH_4VO_3$ | (0.033 mole V) |
|---|---|---|
| 2.1 g. | $H_3BO_3$ | (0.033 mole B) |
| 13.5 g. | $Fe(NO_3)_3 \cdot 9H_2O$ | (0.033 mole Fe) |
| 14.5 g. | $Sb_2O_3$ | (0.1 mole Sb) |
| 58 cc. | $HNO_3$ | (70 percent by weight aqueous solution) |
| 70.6 g. | $(NH_4)_6Mo_7O_{24} \cdot 4H_2O$ | (0.4 mole Mo) |
| 67.2 g. | Ludox AS | (30 percent aqueous solution of $SiO_2$) |

The final catalyst was dried and heat-treated at 800° F for 16 hours and at 1200° F for 19 hours. The surface area of the catalyst was 24 square meters per gram.

N-butane was converted to maleic anhydride according to the procedure described in Example I using this catalyst. A single pass conversion of 18.1 mole percent (30.6 percent by weight) of maleic anhydride was achieved after 5.0 hours on stream.

EXAMPLE VI

A catalyst composed of 80 percent by weight of $PFe_2Sb_3Mo_{12}O_{49}$ and 20 percent by weight of $SiO_2$ was prepared according to Example I from the following materials:

| 27.0 g. | $Fe(NO_3)_3 \cdot 9H_2O$ | (0.067 mole Fe) |
|---|---|---|
| 14.5 g. | $Sb_2O_3$ | (0.100 mole Sb) |
| 60 cc. | $HNO_3$ | (70 percent by weight aqueous solution) |
| 70.6 g. | $(NH_4)_6Mo_7O_{24} \cdot 4H_2O$ | (0.400 mole Mo) |
| 3.8 g. | 85 percent $H_3PO_4$ | (0.033 mole P) |
| 67.4 g. | Ludox AS | (30 percent aqueous solution of $SiO_2$) |

The dried catalyst was heat-treated at 800° F for 16 hours and at 1200° F for 3 hours.

Maleic anhydride was prepared from n-butane using the catalyst of this example in accordance with the procedure of Example I. A single pass yield of 11.8 mole percent (20.0 percent by weight) was observed for maleic anhydride after 1 hour on stream.

EXAMPLE VII

A catalyst composed of 80 percent by weight of Ti-$FeSb_3Mo_6O_{29}$ and 20 percent by weight of $SiO_2$ was prepared according to Example I from the following materials:

| 4.0 g. | $TiO_2$ | (0.05 mole Ti) |
|---|---|---|
| 20.2 g. | $Fe(NO_3)_3 \cdot 9H_2O$ | (0.05 mole Fe) |
| 21.8 g. | $Sb_2O_3$ | (0.15 mole Sb) |
| 88 cc. | $HNO_3$ | (70 percent by weight aqueous solution) |
| 62.7 g. | Ludox AS | (30 percent aqueous solution of $SiO_2$) |
| 53.0 g. | $(NH_4)_6Mo_7O_{24} \cdot 4H_2O$ | (0.30 mole Mo) |

The dried catalyst was heat-treated in air at 800° F for 16 hours and at 1200° F in air for 3 hours.

N-butane was converted to maleic anhydride over the catalyst of this example according to the procedure of Example I. A single pass conversion of 12.8 mole percent (21.6 percent by weight) for maleic anhydride was observed after 1 hour on stream.

EXAMPLE VIII

A catalyst composed of 80 percent by weight of $PFeVSb_3Mo_{12}O_{50}$ and 20 percent by weight of $SiO_2$ was prepared by the procedure of Example VI except that $NH_4VO_3$ was included in the proper preparation.

N-butane was converted to maleic anhydride according to the procedure of Example I using the foregoing catalyst. A single pass conversion of 10.9 mole percent (18.4 percent by weight) of maleic anhydride was achieved.

EXAMPLE IX

A catalyst composed of 80 percent by weight of $BFe_2Sb_3Mo_{12}O_{48}$ and 20 percent by weight of $SiO_2$ was prepared according to a procedure like that described in Example V.

N-butane was converted to maleic anhydride according to the procedure described in Example I using the foregoing catalyst. A single pass conversion of 11.3 mole percent (19.1 percent by weight) of maleic anhydride was achieved.

EXAMPLE X

A catalyst composed of 80 percent by weight of Mo $FeVSb_6O_{22}$ and 20 percent by weight of $SiO_2$ was prepared by a procedure similar to that described in Example I.

N-butane was converted to maleic anhydride with the foregoing catalyst according to the procedure described in Example I. A single pass conversion of 12.7 mole percent (21.5 percent by weight) of maleic anhydride was achieved.

EXAMPLE XI

A catalyst composed of 80 percent by weight of Te-$FeVsb_3Mo_{12}O_{51}$ and 20 percent by weight of $SiO_2$ was prepared by a procedure similar to that described in Example I.

N-butane was converted to maleic anhydride with the foregoing catalyst according to the procedure described in Example I. A single pass conversion of 17.1 mole percent (28.9 percent by weight) of maleic anhydride was achieved.

EXAMPLE XII

A catalyst composed of 80 percent by weight of $Bi_{0.5}FeVSb_3Mo_{12}O_{49}$ and 20 percent by weight of $SiO_2$ was prepared by a procedure similar to that described in Example I.

N-butane was converted to maleic anhydride with the foregoing catalyst according to the procedure described in Example I. A single pass conversion of 14.7 mole percent (24.8 percent by weight conversion) of n-butane to maleic anhydride was achieved.

EXAMPLE XIII

A catalyst which was free of any carrier and had the composition of 100 percent by weight of $FeVSb_3Mo_{1.2}O_{48}$ was prepared by the procedure of Example I except that the use of $SiO_2$ sol was eliminated.

N-butane was converted to maleic anhydride with the foregoing catalyst according to the procedure of Example I. A single pass conversion of n-butane to maleic anhydride of 13.9 mole percent (23.6 percent by weight) was achieved.

We claim:

1. A process for the production of maleic anhydride by the oxidation of n-butane with molecular oxygen or a molecular oxygen-containing gas at a reaction temperature of 300° C to 600° C, in the presence of a catalyst described by the formula $$A_a B_b Sb_c Mo_d O_e$$

wherein
- A is at least one member selected from the group consisting of Fe and V;
- B is at least one member selected from the group consisting of Al, Cr, Co, Ni, Cu, Bi, Te, B, P, Ti and W;
- $a$ is a number from 0.1 to 6;
- $b$ is a number from 0 to 3;
- $c$ is a number from 0.1 to 12;
- $d$ is a number from 12 to 1;
- $e$ is a number determined by the valence requirements of the combined elements other than oxygen present in the catalyst.

2. The process of claim 1 wherein the catalyst is supported on a carrier material selected from the group consisting of silica, alumina, zirconia, calcium-stabilized zirconia, thoria, boron phosphate, silicon carbide, pumice, clay, diatomaceous earth and titania.

3. The process of claim 1 where there is included in the mixture from 0 to 50 moles of steam per mole of the n-butane.

4. The process of claim 1 carried out at an apparent contact time of from 0.1 to 50 seconds.

5. The process of claim 1 wherein A is vanadium.

6. The process of claim 1 wherein A is vanadium and iron.

7. The process of claim 1 wherein the catalyst is $VFeSb_3Mo_{12}O_{48}$.

8. The process of claim 1 wherein the catalyst is $Fe_2Sb_3Mo_{12}O_{47}$.

9. The process of claim 1 wherein the catalyst is $V_2Sb_3Mo_{12}O_{49}$.

10. The process of claim 1 wherein the catalyst is $Mo_2FeVSb_6O_{25}$.

11. The process of claim 1 wherein the catalyst is $BFeVSb_3Mo_{12}O_{49}$.